United States Patent [19]

Feldman

[11] 4,002,172
[45] Jan. 11, 1977

[54] DIAPER HAVING TAB FASTENER WITH CENTRAL FLAP

[75] Inventor: Mark I. Feldman, Chicago, Ill.

[73] Assignee: Johnson & Johnson, N.J.

[22] Filed: Dec. 19, 1975

[21] Appl. No.: 642,284

[52] U.S. Cl. .................................. 128/284; 128/287
[51] Int. Cl.² .................. A61F 13/16; A41B 13/02
[58] Field of Search ............................ 128/284, 287

[56] References Cited
UNITED STATES PATENTS

| | | | |
|---|---|---|---|
| 3,646,937 | 3/1972 | Gellert | 128/287 |
| 3,948,258 | 4/1976 | Karami | 128/287 |

*Primary Examiner*—Aldrich F. Medbery

[57] ABSTRACT

A disposable diaper having a facing sheet defining a diaper inside surface for direction toward an infant and a backing sheet defining a diaper outside surface is provided with adhesive tabs which are slit within the perimetric limits thereof to form a central flap spaced from the edges of the tab. The tab includes a free end and a fixed end. An adhesive coating is provided on at least one face of the flap, free end and fixed end. The fixed end is permanently attached to the diaper backing sheet and the flap is permanently attached to the facing sheet by means of the respective adhesive coatings so that stresses exerted on the tab are distributed to both the facing sheet and the backing sheet when the diaper is secured about an infant.

12 Claims, 9 Drawing Figures

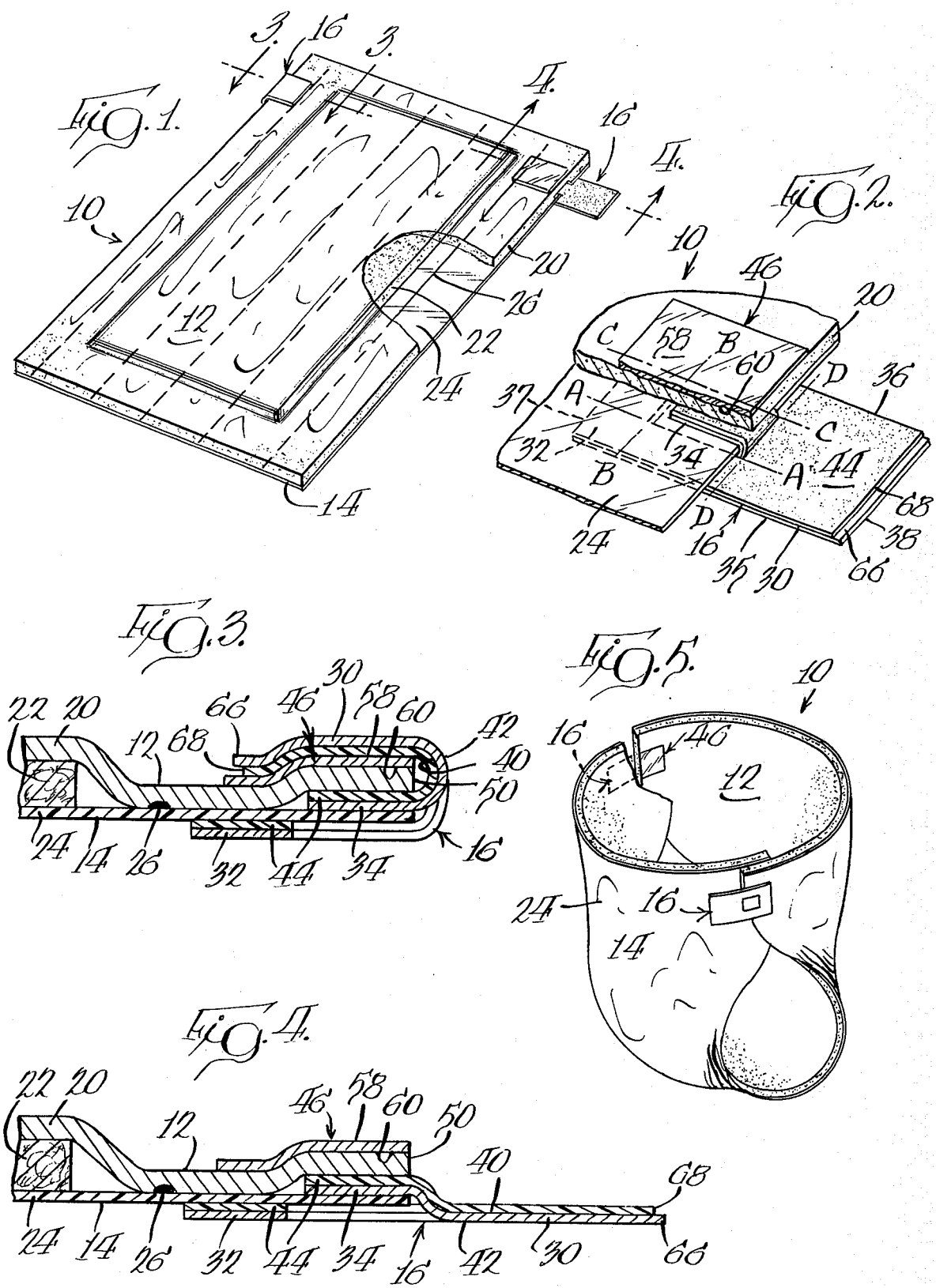

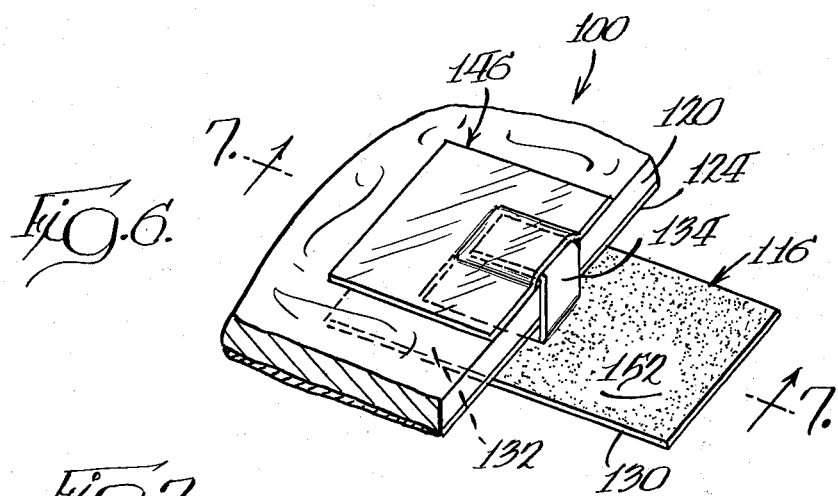
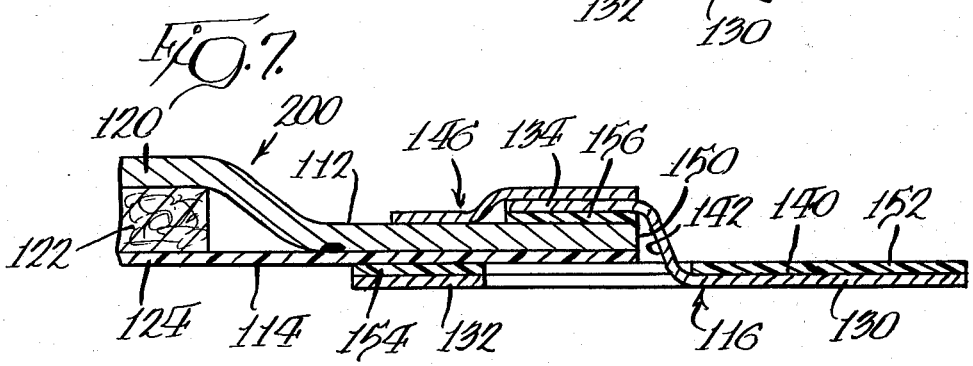
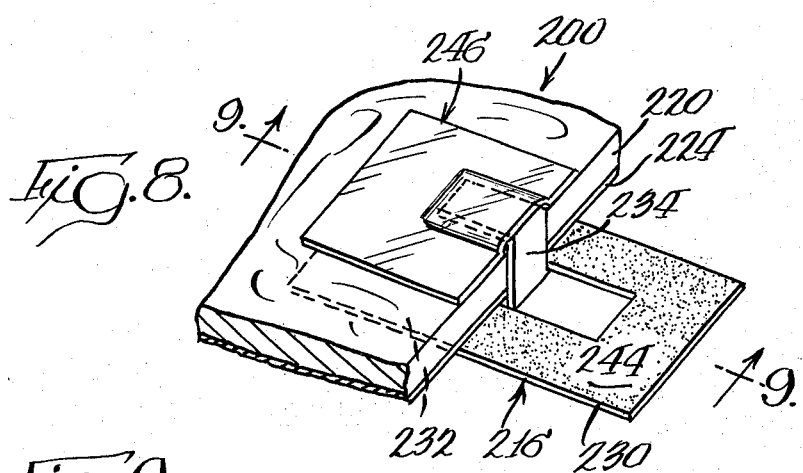
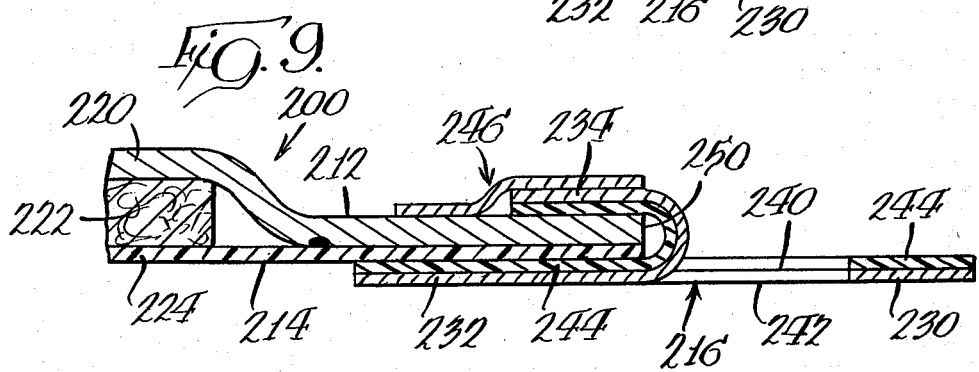

DIAPER HAVING TAB FASTENER WITH CENTRAL FLAP

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,646,937 to Gellert teaches a fastening tab which is provided with a release surface permanently bonded primarily to the inside surface of the diaper. One of the drawbacks of the Gellert arrangement is that in use the adhesive tape fasteners are permanently attached to only one surface of the diaper, generally the outside surface of the backing sheet, and thus the bond between one end of the tape fastener and the diaper backing sheet is subjected to all of the stresses exerted on the tape fastener during securement or as the infant moves about.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric, may tear the facing fabric upon separation therefrom.

U.S. Pat. No. 3,776,234 to Hoey proposes to fold the tab over on itself at the diaper's edge and to adhesively attach a portion of the folded-over tab segment to an inwardly-folded margin of the diaper backing sheet in order to keep the tab flat against the diaper and thus from interfering with the manufacturing machinery and with the subsquent folding and packaging operations. This requires that the edge of the diaper backing sheet be folded over to present an attachment surface at the front or inside of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcng tape portion is attached to the opposite side of first container part. The free end of the main tape portion is adapted for attachment to a second container part which is to be secured to the first container part. Thus, the Hamaguchi et al. patent requires two specially interconnected tape portions. Moreover, the turned up end of the reinforcing tape portion causes the folded configuration of the sealing tape to be somewhat bulky.

The adhesive fastener disclosed in U.S. Pat. No. 3,833,456 to Read et al. can also be attached to both the front and back surfaces of a diaper to provide for force distribution over both surfaces. This particular fastener comprises two co-extensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially coextensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper, but has the disadvantage in that each fastener is comprised of two or more separate tape segments which are joined together so as to produce a common area of joinder for both fastener anchoring legs and the fastener securing portion, thereby adding complexities and expense to the manufacturing process, as well as requiring careful positioning during diaper manufacture.

SUMMARY OF THE INVENTION

According to the present invention, a disposable diaper is provided with an integral adhesive tape tab segment having a central flap, on each side of the diaper to secure the diaper about an infant. The diaper includes a facing sheet defining a diaper inside surface for direction toward an infant and a bacing sheet defining a diaper outside surface.

To form the central flap, each tab segment is slit within the perimetric limits thereof at locations spaced from the edges of the tab. The tab segment also includes a fixed end and a free end. Adhesive coatings are provided on at least one face of the flap, the free end and the fixed end. By means of the adhesive coatings, the fixed end of the tab is permanently attached to the diaper backing sheet and the flap is permanently attached to the diaper facing sheet so that stresses exerted on the tab when the diaper is secured about an infant are distributed to both the facing sheet and the backing sheet.

A release means is provided for engagement with the adhesive coating on the free end of the tab, and preferably is carried by the diaper at a marginal location thereon. The free end is movable from a folded-over storage position in which the free end is releasably adhered to the release means to an extended working position in which the adhesive-coated free end is available for use in securing the diaper about an infant.

In one embodiment, the adhesive coatings on the flap, the free end and the fixed end together comprise a substantially continuous adhesive coating on one face of the tab. The slits which define the flap are on the same end of the tab as the fixed end. The fixed end is attached to the backing sheet on the diaper outside surface, and the flap is interposed between the facing and backing sheets and is permanently attached to the facing sheet.

In another embodiment, the adhesive coatings on the flap, free end and fixed end together comprise a substantially continuous adhesive coating on one face of the tab, but the slits which define the flap are on the same end of the tab as the free end. The fixed end is attached to the diaper backing sheet on the diaper outside surface, and the flap is folded over the facing sheet and is permanently attached to the facing sheet on the diaper inside surface.

Still another embodiment is disclosed in which the slits which define the flap are on the same end of the tab as the fixed end. However, the adhesive coatings on the free end and fixed end are on one face of the tab, while the adhesive coating on the flap is on the opposite face of the tab. The fixed end is permanently attached to the backing sheet on the diaper outside surface, and the flap is permanently attached to the facing sheet on the diaper inside surface.

In all of the embodiments, the peripheral edges of the tab are smooth and uncut to strengthen the tab. The tabs remain substantially flat against the diaper when in the folded configuration, do not interfere with the diaper manufacturing machinery and the subsequent folding and packaging operations, and in use provide good securement of the tab fastener to the diaper. Additional features of this invention include the utilization of an integral tape tab which is relatively easy to use and which provides permanent attachment of the tab to both the diaper facing sheet and backing sheet so that when stress is imposed on the free end which fastens the diaper, the stress is distributed between the facing sheet and the bacing sheet, thereby reducing the possibility of undesirable rupture of the backing sheet.

BRIEF DESCRIPTION OF THE DRAWINGS

FIG. 1 is a perspective view, partially broken away to show interior detail, of an open unfolded diaper in accordance with one of the embodiments of this invention;

FIG. 2 is an enlarged fragmentary perspective view, partially broken away, of a portion of the diaper of FIG. 1;

FIG. 3 is an enlarged fragmentary cross-sectional view of the diaper of FIG. 1 taken along plane 3—3;

FIG. 4 is an enlarged fragmentary cross-sectional view of the diaper of FIG. 1 taken along plane 4—4;

FIG. 5 is a perspective view, partially broken away, of the diaper of FIG. 1 in a configuration assumed by the diaper when placed about an infant;

FIG. 6 is a fragmentary perspective view, similar to FIG. 2, and illustrating another embodiment of this invention;

FIG. 7 is an enlarged fragmentary cross-sectional view of the diaper of FIG. 6 taken along plane 7—7;

FIG. 8 is a fragmentary perspective view, similar to FIGS. 2 and 6, and illustrating another embodiment of this invention; and FIG. 9 is an enlarged fragmentary cross-sectional view of the diaper of FIG. 8 taken along plane 9—9.

DESCRIPTION OF THE PREFERRED EMBODIMENTS

In the following description, two digit numerals are used to refer to the embodiment illustrated in FIGS. 1–5, three digit numerals in the one hundred series are used to refer to the embodiment illustrated in FIGS. 6 and 7, and three digit numerals in the two hundred series are used to refer to the embodiment illustrated in FIGS. 8 and 9. The same last two digits in each numeral designate similar elements in the various embodiments.

Disposable diaper 10, illustrated in FIGS. 1 and 5, is of substantially quadrilateral configuration and presents inside surface 12 for direction toward an infant and outside surface 14 for direction away from the infant. Adhesive tab fastener means such as tab 16 is attached to diaper 10 at a marginal location for securing diaper 10 about an infant. As described in greater detail below, tab 16 is movable from a folded-over storage position illustrated in FIG. 3 to a working position which is illustrated in FIG. 4.

Referring to FIGS. 1–5, diaper 10 comprises moisture-pervious facing sheet 20 which defines diaper inside surface 12, overlying a moisture-retaining absorbent pad 22, and backing sheet 24 which is made of a moisture-impervious material and defines diaper outside surface 14. Absorbent pad 22 can be somewhat smaller than the backing sheet 24 and is centrally disposed thereon; however, absorbent pad 22 can be made coextensive with backing sheet 24, if desired. Facing sheet 20 is substantially coextensive with backing sheet 24. Both the facing sheet 20 and pad 22 can be anchored to the backing sheet 24 by mans of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2–4, tab 16 is an integral elongated tape segment having free working end portion 30 and fixed end portion 32 which is attached to a marginal location of the diaper. As best shown in FIG. 2, tab 16 is slit along lines A—A, B—B, and C—C to form a central flap 34 which is spaced from the transverse edges 35, 36 and longitudinal edges 37, 38 of tab 16. Flap 34 preferably is positioned about midway between transverse edges 35, 36 and has a width of about one half the width of tab 16 and a length of about one fourth the length of tab 16. The slits which define flap 34 are on the same end of tab 16 as fixed end 32 so that fixed end 32 is generally U-shaped and free end 30 is generally rectangular. If desired, flap 34 can be folded about line D—D. Tab 16 has a first face 40 which faces in the same direction as diaper inside surface 12 when tab 16 is in the working position, and an opposite second face 42 (FIGS. 3 and 4).

Free end 30, fixed end 32 and flap 34 are provided with adhesive coatings on one face thereof. In the embodiment illustrated in FIGS. 1–5, the adhesive coatings on free end 30, fixed end 32 and flap 34 together comprise a substantially continuous adhesive coating 44 on first face 40 of tab 16. Since the adhesive coating one free end 30 is desirably pressure-sensitive, adhesive coating 44 preferably comprises a pressure-sensitive adhesive coating.

Tab 16 is permanently attached to facing sheet 20 and backing sheet 24 at a marginal location of the diaper 10. In the embodiment illustrated in FIGS. 2–4 a marginal portion of backing sheet 24 is received between fixed end 32 and flap 34. Fixed end 32 is adhesively attached to backing sheet 24 on diaper outside surface 14 by means of adhesive coating 44, and flap 34 is interposed between facing sheet 20 and backing sheet 24, and is adhesively attached to facing sheet 20 by means of adhesive coating 44. Forces exerted on tab 16 are thereby distributed to both the facing sheet 20 and backing sheet 24. Though adhesive coating 44 preferably comprises a continuous pressure-sensitive adhesive coating, the adhesive coating on fixed end 32 and flap 34 can be made of a heat-activated or solvent-activated composition, or the like.

Release means 46 is provided and is adapted to be releasably attached to the portion of adhesive coating 44 on free end 30. The release means msy be carried by diaper 10 at a marginal location thereon to provide a release region facing in the same direction as diaper inside surface 12.

Referring to FIGS. 3 and 4, tab 16 is folded about the longitudinal edge 50 of diaper 10, and end portions 30 and 32 of tab 16 preferably are about equal in length. Free end 30 provides a securement means for fastening diaper 10 about an infant and can be moved from the closed, storage position of FIG. 3 in which the portion of adhesive coating 44 on free end 30 is releasably adhered to release means 46 to the open, working position of FIG. 4 in which portion of adhesive coating 44 on free end 30 is available for use in securing diaper 10 about an infant. The portion of adhesive coating 44 on free end 30 faces in the same direction as diaper inside surface 12 when tab 16 is in the working position.

In the embodiment illustrated in FIGS. 6 and 7, diaper 100 has tab 116 which includes a free end 130, fixed end 132 and central flap 134 which is spaced from the edges of tab 116. Free end 130 is provided with a pressure-sensitive adhesive coating 152 on first face 40 thereof, and fixed end 132 is provided with adhesive coating 154 on first face 140. Flap 134 is provided with adhesive coating 156 on the second face 142 thereof. In this embodiment, a marginal portion of diaper 100 is received between fixed end 132 and flap 134. The slits which define flap 134 are on the same end of tab 116 as fixed end 132, so that fixed end 132 is generally U-shaped and free end 130 is generally rectangular. Fixed end 132 is permanently attached to backing sheet 124 on diaper outside surface 114 by means of adhesive coating 154, and flap 134 is folded about longitudinal edge 150 of diaper 100 and permanently attached to facing sheet 120 on diaper inside surface 112.

Referring to the embodiment illustrated in FIGS. 8 and 9, diaper 200 has tab 216 which includes free end 230, fixed end 232 and central flap 234 which is spaced from the edges of tabs 216. The adhesive coating on free end 230, fixed end 232 and flap 234 may comprise a substantially continuous adhesive coating 244 on the first face 240 of tab 216. The slits which define flap 234 are on the same end of tab 216 as free end 230, so that free end 230 is generally U-shaped and fixed end 232 is generally rectangular. Fixed end 232 is permanently attached to backing sheet 224 on diaper outside surface 214 by means of the portion of adhesive coating 244 on fixed end 232, and flap 234 is folded about longitudinal edge 250 of diaper 200 and permanently attached to facing sheet 220 on diaper inside surface 212 by means of the portion of adhesive coating 244 on flap 234.

In all of the embodiments, an integral elongated tape segment is attached to both facing sheet 20 and backing sheet 24 distribute forces imposed on the tape segment, and the peripheral edges of the tape segment are uninterrupted and uncut to thereby give greater strength to the tape segment. This is accomplished by having the open-ended portion of the U-shaped end of the tab directed towards the rectangular-shaped opposite end of the tab, so that the open portion is surrounded by the rest of the tab. Thus, in the embodiment illustrated in FIGS. 1–7, the slits which define flap 34 are on the same side of tab 16 as fixed end 32 so that fixed end 32 is generally U-shaped and free end 30 is a generally rectangular portion of tab 16; in the embodiment illustrated in FIGS. 8 and 9, free end 30 is generally U-shaped and fixed end 32 is a generally rectangular portion of tab 16.

It is a further feature of the embodiments illustrated in FIGS. 1–5 and 8–9 that the adhesive coatings on free end 30, fixed end 32 and flap 34 may comprise a substantially continuous adhesive coating on one face of tab 16. In the embodiment illustrated in FIGS. 1–5, flap 34 is interposed between facing sheet 20 and backing sheet 24 and is permanently attached to facing sheet, whereas in the embodiments illustrated in FIGS. 6–9 flap 34 is folded over facing sheet 20 and permanently attached to the facing sheet on diaper inside surface 12.

Release means 46 may comprise a release surface or layer, and various embodiments are contemplated in which the release means is provided between portion of adhesive coating 44 on free end 30 and diaper inside surface 12 which is juxtaposed to free end 30 when tab 16 is in the folded-over, closed position. For example, in the embodiment illustrated in FIGS. 2–4, the release surface comprises a ribbon segment or release strip having a release-coated surface on face 58 which provides a release region, and an adhesive coating on opposite face 60 by means of which the release strip is anchored to diaper inside surface 12. The release strip preferably provides a release region of about the same width as tab 16 and substantially coextensive with the portion of adhesive coating 44 on free end 30. However, the release region may have a greater width than tab 16. Release means 46 may alternatively comprise a surface coating of silicone release compound, or the like, on a marginal portion of diaper inside surface 12.

In the embodiments of FIGS. 6–9, where flap 134, 234 is attached to facing sheets 120, 220 on diaper inside surface 112, 212 and has an exposed second face 142, 242 facing in the same direction as the diaper inside surface, (FIGS. 6–9), the ribbon segment or release strip can be anchored to diaper 100, 200 by adhesive attachment to exposed face 142, 242 of flap 134, 234.

It is desirable to provide a gripping means to facilitate separation of free end 30 of tab 16 from the release means preparatory to fastening the diaper about an infant. As is shown in FIGS. 2–4, free end 30 of tab 16 can be provided with a projecting portion 66 which extends beyond outermost margin of edge 68 of adhesive coating 44, whereby outwardly extending portion 66 provides a gripping means for removing free end 30 from the release means when fastening diaper 10 about an infant. Alternatively, release means 46 can be provided with a longitudinal dimension which is greater than the longitudinal dimension of free end 30 to enable a user to more easily grasp free end 30. These and other modifications may be simultaneously used to facilitate gripping the free end 30.

Adhesive tabs suitable for the purpose of the present invention can be made from a wide variety of materials, provided that such materials are sufficiently flexible. Preferred materials for this purpose are polyalkylene webs such as polyethylene sheet, polypropylene sheet and the like. Particularly preferred are webs which are oriented along the narrow dimension of the tab or webs which have filament reinforcements therein.

The pressure-sensitive adhesive layers such as the portion of adhesive coating 44 on free end 30 are provided by applying a coating of a pressure-sensitive adhesive composition known in the art to the appropriate surface of tab 16. This applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, an the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 2,663,348 to Lilois et al.

Facing sheet materials suitable for use in this invention can have fabric weights in the range of about 1 to 5 oz./yd$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in the U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling free end portions 30 away from their temporary engagement with the release means, exposing the portion of adhesive coating 44 along free end 30 which was releasably adhered to release means 46 and separable therefrom. The tabs are then used to secure the diaper in the desired position by simply urging the pressure-sensitive adhesive surfaces in contact with the adjacent outer surface of the diaper. The applied diaper assumes the configuration illustrated in FIG. 5.

The foregoing description and the drawing are illustrative but are not to be taken as limiting. Still other variations and modifications are possible without departing from the spirit and scope of the present invention. For example, flap 34 may be interposed between facing sheet 20 and backing sheet 24 and be provided with an adhesive coating only on first face 42, whereby fixed end 32 and flap 34 are both attached to backing sheet 24 to better distribute stresses through backing sheet 24. Alternatively, flap 34 may be interposed between facing sheet 20 and backing sheet 24 and may be provided with adhesive coatings on both faces 40, 42 thereof, whereby fixed end 32 and flap 34 are both attached to backing sheet 24 and flap 34 is simultaneously attached to facing sheet 20. Moreover, the width, length, shape and position of flap 34 can be varied as desired.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:

an integral elongated tape segment comprising a free working end and a fixed end attached to said diaper at a marginal location thereof, said tape segment being slit to form a central flap within the perimetric limits and spaced from the edges of said tape segment;

an adhesive coating on at least one face of said flap, said free end and said fixed end, said adhesive coating on one face of said free end being pressure-sensitive; and release means for engagement with said adhesive coating on said free end;

said fixed end being permanently attached to said backing sheet and said flap being permanently attached to said facing sheet by means of said adhesive coatings; and said free end being separable from said release means to make said adhesive-coated free end of said tape segment available for use in securing said diaper about an infant.

2. The disposable diaper as defined as in claim 1 wherein said adhesive coatings on said free end, said fixed end and said flap are pressure-sensitive and together provide a substantially continuous adhesive coating on one face of said tape segment, and wherein said fixed end is permanently attached to said backing sheet on the diaper outside surface.

3. The disposable diaper as defined in claim 1 wherein said adhesive coatings on said free end, said fixed end and said flap are pressure-sensitive and together provide a substantially continuous adhesive coating on one face of said tape segment, wherein said flap is folded over said facing sheet and permanently attached to said facing sheet on the diaper inside surface, and wherein said fixed end is permanently attached to said backing sheet on the diaper outside surface.

4. The disposable diaper as defined in claim 1 wherein said adhesive coatings on said free end and said fixed end are on one face of said tape segment, and said adhesive coating on said flap is provided on the opposite face of said tape segment, and wherein said fixed end is permanently attached to said backing sheet on the diaper outside surface and said flap is permanently attached to said facing sheet on the diaper inside surface.

5. The disposable diaper as defined in claim 1 wherein said tape segment has a pair of transverse edges and said flap is positioned about midway between said transverse edges.

6. The disposable diaper as defined in claim 1 wherein said flap has a width of about one half the width of said tape segment and a length of about one fourth the length of said tape segment.

7. The disposable diaper as defined in claim 1 wherein said release means is carried by said diaper at a marginal location thereon and provides a release region facing in the same direction as said diaper inside surface;

said free end being movable from a folded-over storage position wherein said free end is releasably adhered to said release region to a working position wherein said adhesive-coated free end of said tape segment is available for use in securing said diaper about an infant.

8. The disposable diaper as defined in claim 7 wherein said release means comprises a ribbon segment carried by said diaper and provided with a release coating substantially coextensive with said free end of said tape segment and facing in the same direction as said diaper inside surface.

9. The disposable diaper as defined in claim 7 wherein said release means is a release coating on a portion of said diaper inside surface.

10. The disposable diaper as defined in claim 9 wherein said release coating comprises a silicone release compound.

11. The disposable diaper as defined in claim 7 wherein a portion of said free end projects beyond the outermost edge of said adhesive coating on said free end, whereby said projecting portion provides a gripping means for separating said tape segment from said release means when fastening said diaper about said infant.

12. The disposable diaper as defined in claim 7 wherein said release means has a width greater than the width of said tape segment and a longitudinal dimension greater than said free end to facilitate gripping said free end for separating said tape segment from said release means when fastening said diaper about said infant.

* * * * *